United States Patent [19]
Peters

[11] Patent Number: 5,139,476
[45] Date of Patent: Aug. 18, 1992

[54] ORTHOTIC KNEE WRAP

[75] Inventor: Helena Peters, Bromma, Sweden

[73] Assignee: Camp International, Inc., Jackson, Mich.

[21] Appl. No.: 691,992

[22] Filed: Apr. 26, 1991

[51] Int. Cl.$^5$ .............................................. A61F 5/00
[52] U.S. Cl. ........................................ 602/26; 602/23
[58] Field of Search .................. 128/80 C, 165, 87 R; 2/22, 24

[56] References Cited

U.S. PATENT DOCUMENTS

| | | |
|---|---|---|
| 3,786,804 | 1/1974 | Lewis . |
| 3,804,084 | 4/1974 | Lehman . |
| 3,831,467 | 8/1974 | Moore . |
| 3,935,858 | 2/1976 | Harroff . |
| 4,013,070 | 3/1977 | Harroff . |
| 4,084,586 | 4/1978 | Hettick . |
| 4,296,744 | 10/1981 | Palumbo ............................. 128/165 |
| 4,423,720 | 1/1984 | Meier et al. . |
| 4,724,831 | 2/1988 | Huntjens ........................... 128/80 C |
| 4,832,010 | 5/1989 | Lerman ............................. 128/80 C |
| 4,961,418 | 10/1990 | McLaurin-Smith ................ 128/165 |
| 5,024,216 | 6/1991 | Shiono ..................................... 2/24 |

Primary Examiner—Richard J. Apley
Assistant Examiner—Lynne A. Reichard
Attorney, Agent, or Firm—Price, Heneveld, Cooper, DeWitt & Litton

[57] ABSTRACT

There is disclosed a knee wrap support adapted to be wrapped about the knee comprising a body portion preferably formed of an elasticized fabric laminate. Wrap strips extend away from the main body portion of the support. Each encircling wrap is of sufficient length to encircle the entire thigh or calf, as the case may be, at least once. The outer surface of the support preferably comprises an elasticized fabric having a surface comprising looped fastening means. The inner surface is adapted to be worn next to the skin and preferably comprises an elasticized cotton fabric. The inner surface of the free end of each encircling wrap strip is provided with hooked fastening for releasably engaging to outer surface looped fastening means, preferably to the looped fastening means on the outer surface of the proximal and distal wraps. The support includes a patella opening medially located in the main body and a pair of reinforcing strips comprising reinforcing stays which are vertically disposed and oriented between the patella opening and the apexes of the C-shaped concave recesses, on either side of the patella opening.

12 Claims, 1 Drawing Sheet

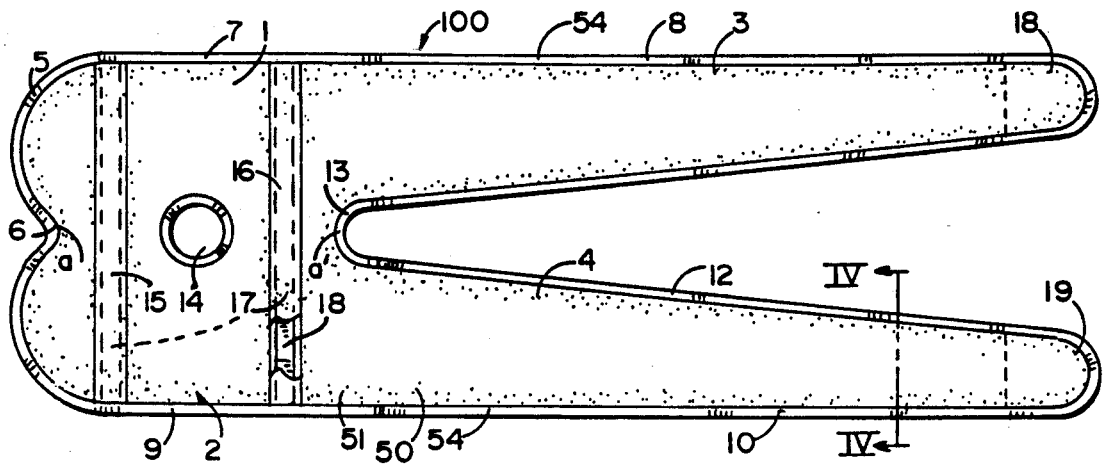
FIG. 1
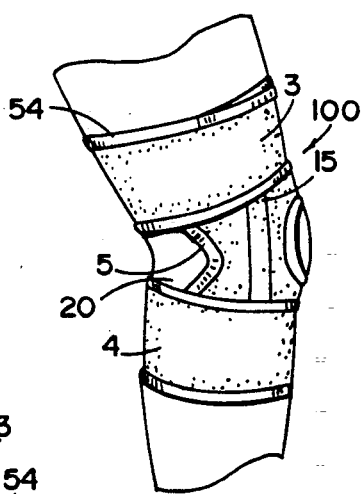
FIG. 2
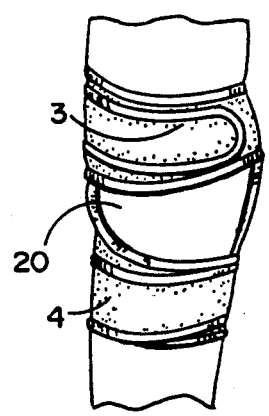
FIG. 4
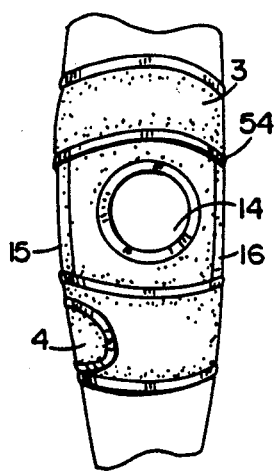
FIG. 3
FIG. 5

ORTHOTIC KNEE WRAP

BACKGROUND OF THE INVENTION

This invention relates to a knee support wrap and, in particular, to a knee support wrap adapted to prevent injuries to the knee, provide support for an already injured or weakened knee and is capable of stabilizing the knee without impairing circulation and normal flexibility.

The human knee is subjected to a wide variety of compressive, bending, twisting and lateral forces, particularly, when the individual is active in physically strenuous activities. Injuries to the knee are quite common among athletes and the general public. The most common occurring injuries relate to stretching or tearing of the various knee ligaments, injury to the cartilage and particular surfaces of the knee joint, and fractures. These type injuries are quite troublesome, because of the mechanical characteristics of the human limb joint. Furthermore, the repetitive, abnormal lateral excursions which cause abnormal shearing forces, frequently lead to early, accelerated and progressive degenerative changes in the bones of the joint.

Individuals who have sustained knee injuries, who have had operations to remove cartilage, or who have weak knee joints from causes such as arthritis primarily need protection against lateral motion of the knee in a direction transverse in the plane of flexion and extension, such as might be caused by a blow to the side of the knee. At the same time, a suitable knee support should not interfere with the normal flexion and extension of the leg, particularly if the wearer has difficulty bending over. The support should protect the knee against sideways motions during both flexion and extension. As the healing process of a knee injury progresses, it has been difficult to provide support and bracing which is adjustable to meet the condition of a wearer from the initial several days of swelling, to the following days when swelling decreases gradually, and, later, over the ensuing weeks when gradually less bracing and support of the knees are required.

A frequently employed approach to support a weakened knee has been to apply adhesive tape around the joint in order to provide some measure of protection and added strength. This approach is expensive since it requires the time of a trainer, requires someone with knowledge of how to properly wrap the adhesive tape and uses a significant amount of tape which is not reusable. Also, it leads to discomfort arising from impaired circulation and during the removal of the tape from the skin. Other supports include various elastic sleeves, some using stiffeners to provide additional strength to the support in an effort to assist the wearer. Other prior art devices include knee supports and braces characterized by hinges on the lateral and medial side of the knee, some have been characterized by straps, and some have employed belts or have utilized spiral wrappings extending above and below the kneecap.

SUMMARY OF THE INVENTION

In accordance with the present invention there is provided a unitary knee support comprising a generally U-shaped, flexible, resilient body adapted to anatomically conform to the body member. The support is provided with integral encircling straps. The encircling straps are each sufficiently long so as to encompass the thigh or calf area, as the case may be, at least once to ensure that a desired degree of stability is obtained. The encircling straps are shaped such that when the support is properly wrapped about the knee, a posterior opening is formed which eliminates pressure and inhibits material bunching in the sensitive popliteal area.

Other objects and many of the attendant advantages of this invention will be readily appreciated as the same become better understood by reference to the following detailed description when considered in connection with the accompanying drawings wherein:

BRIEF DESCRIPTION OF THE DRAWINGS

FIG. 1 is a plan view of the cutout portion of the wrap of this invention;

FIG. 2 is a side-elevational view of the knee support of this invention mounted on a knee;

FIG. 3 is a front elevational view of the knee support mounted on a knee;

FIG. 4 is a cross-sectional view taken along the plane IV—IV of FIG. 2; and

FIG. 5 is a rear-elevational view of the wrap mounted on a knee and showing the opening over the popliteal area.

DESCRIPTION OF THE PREFERRED EMBODIMENTS

In the preferred embodiments, the knee wrap support 100 is also provided with medial and lateral stays 18, which are preferably semi-rigid, flexible flat spiral coil metal stays but can be of any shape or formed from any material, such as plastics, which have been commonly used for this purpose. The knee supports 100 are useable on either knee without modification.

In use, the support 100 is placed on the leg with the patella opening 14 at the knee. In this position, the support 100 is approximately centered in the knee area with the medial and lateral stays 18 being located substantially along and on each side of the center line of the leg. Once properly located, the upper and lower encircling straps 3 and 4 are wrapped about the thigh and calf, respectively, forming a popliteal opening at the rear of the leg. The length of the encircling straps 3 and 4 is sufficient to encircle the lower thigh and upper calf at least once, and the free ends of the legs are attached either to the outer surface 51 of the body or, preferably, the outer surface 51 of the encircling strap, as the case may be. As the encircling straps 3 and 4 extend over the medial and lateral stays 7 at least once, an adjustable, substantially equally distributed, effective compression and firm stabilization of the stays is achieved to provide the required knee stability. It will be appreciated that compression may be adjusted to a desired level by increasing or decreasing the tightness of the encircling legs 3 and 4.

The knee wrap support of the invention is formed from a resilient flexible material comprising an exposed outer surface or layer and an inner layer or surface adapted to be worn next to the body area. More particularly, the supports of this invention can be formed from substantially any natural or synthetic material, including both inelastic and elastic materials, having sufficient flexibility and resiliency to enable the support to anatomically conform to the body member to which it is applied. In addition, the supports include mutually intercooperating connector means comprising loop keeper means on at least a portion of the outer surface of the support and a companionate array of hook keeper means on at least a portion of the inner surface of the support which confront the loop keeper means when both keeper means are in an overlying relationship on the supports; the hook means being adapted in response to pressure against the loop means to intermesh with the loop means and releasably cling to the loop means, to be separated therefrom in response to a peeling quick yanking force.

The resilient flexible natural or synthetic materials suitable for use in the practice of the invention include fabrics made from inelastic fibers such as nylon fibers, polyester fibers, cotton fibers and the like; elastomers such as natural rubber, neoprene rubber and the like; and elasticized fibers comprising a blend of at least one inelastic fiber, such as nylon, polyester, cotton and the like and at least one elastomeric fiber, such as those sold under the trademark Lycra, and including combinations of two or more natural and/or synthetic materials, generally in the form of a laminated structure.

The preferred material comprises a flexible resilient elasticized fabric laminate comprising an outer elasticized fabric layer, an open-cell polymeric foam core and an inner or proximal elasticized fabric layer. The foam core is coextensive with and adhered to both inner and outer layers. The laminate is stretchable in all directions. The inner and outer layers comprise elasticized fabrics having substantially the same degree of stretch in all directions. The outer elasticized fabric layer is preferably a high moisture absorbent fabric comprising a blend of at least one inelastic fiber and at least one elastic fiber, with a blend of inelastic polyamide and elastic polyurethane being currently preferred. The outer surface has a brushed felt-like texture comprising myriad upstanding and relatively free fiber loop fastening means. The inner layer is preferably a lower moisture absorbent but good wicking fabric comprising an elasticized cotton fabric comprising a blend of cotton and at least one elastic fiber, preferably an elastic polyurethane fiber. The polymeric foam core is an open-celled cellular material which is preferably a polyurethane or polystyrene foam and is most preferably a polyethylene foam. Currently, a preferred composite comprises 35 weight percent polyamide, 42 weight percent cotton, 18 weight percent polyurethane elastic fiber and 5 weight percent open-cell polyethylene foam, based on total weight of the composite. The provision of elasticized fibers and fabrics from different natural and synthetic fibers is well-known in the art, and there is no need for elaboration. The composite is lightweight, stretchable to anatomically conform to the body member, durable and easily laundered in home washing machines. Drip-drying is the preferred method of drying laundered supports. The high-absorbent elasticized outer layer, the open-cell polymeric foam core and the low-absorbent elasticized inner layer cooperatively provide a breathable composite which aids in the transfer of moisture, such as perspiration from the wearer's body to the outer surface of the outer or exposed layer, which has sufficient porosity to enable moisture to be wicked from the body to the outer surface of the support. The elasticized cotton inner layer ensures dryness, provides a comfortable feel against the body and a feeling of soothing warmth for injured and arthritic joints when engaging in strenuous activities while minimizing heat buildup during such activities.

Referring now to the drawings and particularly FIG. 1, the knee wrap 100 of the invention comprises a material 1 (FIG. 4) cut out to form a main body 2 from which integrally extend the legs 3 and 4. The main body and legs are preferably cut in one piece and constructed of an elasticized fabric laminate 50, see FIG. 4. Outer surface 51 comprises an elasticized fiber having a looped texture adapted to releasably engage with hook fasteners. The elasticized fabric comprises an inelastic fiber - elastic fiber blend, with a polyamide-elastomeric fiber blend being particularly preferred. Inner surface 53 (the side next to the skin) comprises an elasticized, cotton fiber formed from a blend comprising cotton fiber and at least one elastic fiber, with elastomeric polyurethane being the preferred elastic fiber. The laminate 50 also includes a core 52 comprising a thin (0.1–0.3 inch) open-celled polymeric foamed body, with polyethylene, polystyrene and polyurethane open-celled foams being particularly preferred. A currently preferred construction comprises 35 weight percent polyamide, 42 weight percent cotton, 18 weight percent elastomeric polyurethane and 5 weight percent open-celled polyethylene foam, based on total weight of elasticized fabric laminate. The edges of the composite are bound by a sewn or stitched elastic binding 54.

The material 1 is shown with outer face 51 appearing to the viewer. The cutout material 1 includes a body portion 2 from which extend substantially parallel legs or straps 3 and 4 having a sufficient length to permit the legs to be wrapped at least once, more preferably about 1½ times, about the lower thigh and the upper calf of the user adjacent the knee. Hook fastener patches 18 and 19 are sewn on the inner surface at the free end of each leg. Each leg, after being wrapped about the user's limb, is fastened to the outer surface 51 of body 2 or, preferably, to the outer surface 51 of the leg.

Body portion 2 includes a side edge 5 which includes a medially located U-shaped convex recess 6. Body portion 2 also includes a top edge 7 which is substantially straight and merges into substantially straight top edge 8 of leg 3 and a substantially straight bottom edge 9 which merges into bottom edge 10 of leg 4. The inner leg edges 11 and 12, respectively, of legs 3 and 4, respectively, taper inwardly towards body portion 2 to terminate in a U-shaped convex recess 13. The taper is such that a portion of recess 13 is a substantial mirror image of recess 6. Body portion 2 also includes patella opening 14 which is located substantially half way between top edge 7 and top edge 9 and substantially midway between the apexes a and a' of recesses 6 and 13. Base portion 2 also carries reinforcing strips 15 and 16 which are of substantially identical construction and include a sewn in pocket 17 which carries a reinforcing stay 18. Stay 18 is preferably of the flattened metal coil spiral type wherein the stay is relatively flexible lengthwise to conform to the configuration of the knee when the support is applied, but resists lateral deformation, but can be of plastic or any other material and shape which have been commonly used for this purpose. The stay aids in distributing the compression forces upon the cushion pad when wrapped with legs 3 and 4 to provide substantially equal support and stabilization to both medial and lateral sides of the knee. As noted, each of legs 3 and 4 carry a hook pad 18 and 19, respectively, on the inner surface of each leg for engagement with the looped surface 51.

Reinforcing strip 16 is vertically disposed and extends from top edge 7 to bottom edge 9 and is otherwise located substantially half way between the center line of patella opening 14 and apex a' of recess 13. Reinforcing strip 15 is similarly located, extending vertically between top edge 7 and bottom edge 9 and otherwise located substantially half way between the center of the vertical center line of patella opening 14 and apex a of recess 6. This construction will locate reinforcing strip 16 with its stay 18 along the lateral center line of the leg and reinforcing strip 15 with its stay 18 along the medial center line of the leg when support 100, as shown, is properly located on the right knee of the wearer.

To apply the knee wrap support of the invention to the knee, body member 2 is placed over the knee with the patella of the knee protruding through patella opening 14 (FIGS. 3 and 5). Legs 3 and 4 are then drawn towards the back of the leg and underneath the leg in order that the support may be wrapped in a posterior fashion. It is understood that inner surface 53 of laminate 50 will be disposed towards the wearer's leg. Side edge 5 of support body portion 2 is wrapped to the rear along the inner side of the wearer's knee. Legs 3 and 4 will then be drawn over edge 5. Then leg 3 will be wrapped toward the front of the leg over medial reinforcing strip 15, across the thigh above the patella opening and across lateral reinforcing strip 16. Leg 3 is then securely attached to the upper portion of body portion 1 or, preferably, the outer surface 51 of leg 3 by pressing hook patch 18 against outer surface 51. Most preferably, leg 3 is of sufficient length that it can be drawn around the thigh area at least 1½ times and fastened on the front or lateral side of the leg to the looped surface 51 of leg 3. This provides substantially equally distributed support, compression and stabilization to both medial and lateral sides of the knee and also reduces discomfort, such as chafing on the medial side of the knee and in the popliteal area. It will be appreciated that sufficient tension will be applied to strap 3 during the wrapping in order that a desired amount of compression is applied in the knee area.

In a similar manner, leg 4 is drawn, with the tension required for the desired compression, around the back of the leg over edge 5 and wrapped about the upper portion of the calf below the knee across the bottom portion of reinforcing strips 15 and 16. The hook fastener 19 of leg 4 is attached to the looped outer surface 51, preferably the looped outer surface 51 of leg 4, thereby affixing the support in place upon the knee. Most preferably, leg 4 is of sufficient length that it can be wrapped about the upper calf at least 1½ times and fastened on the front or lateral side of the support to the looped surface 51 of leg 4. This provides substantially equally distributed support, compression and stabilization to both medial and lateral sides of the knee and also reduces discomfort, such as chafing, on the medial side of the knee and in the popliteal area.

The tension with which legs 3 and 4 are drawn around the thigh and calf, respectively, determines the amount of compression which is applied to the member and which produces the desired medial and lateral stability. The proper positioning of side edge 5 towards the rear of the leg, combined with the proper wrapping of legs 3 and 4 around the thigh and calf, respectively, of the leg bring recesses 6 and 13 into positions along opposite side of the knee to create a hinge-like edge which accommodates bending of the knee. Installation of the support is now completed as disclosed in FIGS. 2, 3 and 5.

As disclosed in FIGS. 2 and 5, the wrap provides an open space at the popliteal area behind the knee. As disclosed in FIG. 3, the patella opening is expanded to a larger size than shown in FIG. 1 since tension is applied to the wrap when applied and also bending of the knee causes the patella to protrude through the opening to increase the size of the opening to more nearly the size of the patella. This increase in size of opening 14 is permitted by the ability of the fabric to expand in all directions.

The knee wrap support of the invention is effective in applying a desired substantially equally distributed pressure to the medial and lateral areas of the knee without producing pressure on the patella or excessive constriction of the wearer's leg. The popliteal opening 20 (FIGS. 2 and 5), which is formed by the shape of the material 1, significantly reduces posterior knee binding. The invention allows a free range of motion avoiding unnecessary stress to the knee joint. The adjustable tension control which is permitted by varying the tension with which legs or straps 3 and 4 are drawn about the leg permits the pressures imposed upon the medial and lateral areas of the leg to be accurately adjusted for maximum efficiency and comfort. The support may be quickly applied to the wearer's leg without requiring unusual skill. The construction of the support reduces the need for inventories because the support may be used with either right or left limbs without requiring modification.

It is appreciated that various modifications to the inventive concept may be apparent to those skilled in the art without departing from the spirit and scope of the invention.

The embodiments of the invention in which an exclusive property or privilege is claimed are defined as follows:

1. A knee support wrap adapted to be wrapped about a knee, comprising:
    a flexible resilient integral sheet of elasticized fabric shaped to define an elastic main body portion and a pair of elongated elastic straps integral with said main body portion and made of the same material as said main body portion throughout their length;
    said main body having a width sufficient to extend from top to bottom from the lower region of the thigh to the upper region of the calf;
    said main body portion having a length sufficient to be wrapped about at least the front and side portions of the knee;
    said pair of elongated elastic straps extending from a first end of said main body portion adjacent the bottom and top edges of said main body portion, respectively; and
    each of said straps having a length sufficient to encircle the upper calf and lower thigh regions, respectively, at least once, the width of said straps having a dimension so as to provide a sufficient space between said straps whereby when said support wrap is wrapped around a knee with one strap encircling the lower region of the thigh and the other strap encircling the upper region of the calf an opening is provided between said straps in the popliteal area behind the knee, said wrap being free of a third strap between said pair of straps which would extend over said opening between said pairs of straps.

2. A knee support wrap according to claim 1 wherein said elasticized fabric comprises an inner surface adapted to be placed against the body and an outer exposed surface forming a looped fastening means, and the inner surface at each end of said encircling straps is provided with hooked fastening means adapted to releasably engage the looped fastening means of said outer surface.

3. A knee support wrap according to claim 2, wherein said elasticized fabric is a laminate which includes a core comprising an open-celled polymeric foam.

4. A knee support wrap according to claim 3, wherein said outer exposed surface of said elasticized fabric comprises a blend of at least one inelastic fiber and at least one elastic fiber and said inner surface of said elasticized fabric comprises a blend of cotton fiber and at least one elastic fiber.

5. A knee support wrap according to claim 2 including a pair of elongated reinforcing means secured to said main body portion and extending transversely to the length of said encircling wraps, each of said reinforcing means including a reinforcing stay, one of said reinforcing means being disposed on the medial side of said knee and the other on the lateral side when the wrap is in place on the knee, the attachment of said straps about said knee being adjustable thereby providing adjustable compression and stabilization of the straps.

6. A knee support wrap of claim 1 wherein an end of said main body opposite said first end includes a recess providing an open portion at the side of the knee to accommodate bending of the knee.

7. A knee support wrap according to claim 1 including a pair of elongated reinforcing means secured to said main body portion and extending transversely to the length of said encircling wraps, each of said reinforcing means including a reinforcing stay, one of said reinforcing means being disposed on the medial side of said knee and the other on the lateral side when the wrap is in place on the knee, the attachment of said encircling straps about said knee being adjustable thereby providing adjustable compression and stabilization of the straps.

8. A knee support wrap according to claim 7 in which an opening is provided between said reinforcing stays for receiving the patella of a knee.

9. A knee support wrap according to claim 1 wherein said wrap is stretchable in all directions.

10. A knee support wrap according to claim 1 in which an opening is provided in the central area of said main body portion of receiving a patella of a knee.

11. A knee support wrap of claim 1 in which the peripheral edges of said straps include an outer edge extending substantially in a straight line from said top and bottom edges of said main body portion to the terminal ends of said straps and then is reversed in direction to provide an inner edge extending at an inclined angle to the proximate longitudinal center line of said main body portion thereby providing straps of increasing width from said terminal ends to said main body portion.

12. A knee support wrap of claim 11 in which the other end of said main body portion includes a U-shaped recess; said inner edges of said straps intersecting to form a "U"; said U-shaped recess conforming substantially to a portion of the "U" formed between said inner edges and providing recesses on each side of a knee at a location where the knee bends thereby accommodating the bending of the knee.

* * * * *

UNITED STATES PATENT AND TRADEMARK OFFICE
CERTIFICATE OF CORRECTION

PATENT NO.  : 5,139,476
DATED       : August 18, 1992
INVENTOR(S) : Helena Peters It is certified that error appears in the above-identified patent and that said Letters Patent is hereby corrected as shown below:

```
Column 8, line 12, claim 10;
     "portion of" should be --portion for--.
```

Signed and Sealed this

Twenty-sixth Day of October, 1993

*Attest:*

BRUCE LEHMAN

*Attesting Officer*  *Commissioner of Patents and Trademarks*